US012749185B2

(12) United States Patent
Mostapha et al.

(10) Patent No.: US 12,749,185 B2
(45) Date of Patent: Sep. 29, 2026

(54) ITERATIVE RESTORATION OF CORRUPTED MR IMAGES

(71) Applicant: Siemens Healthineers AG, Forchheim (DE)

(72) Inventors: Mahmoud Mostapha, Princeton, NJ (US); Mariappan S. Nadar, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 266 days.

(21) Appl. No.: 18/470,787

(22) Filed: Sep. 20, 2023

(65) Prior Publication Data

US 2025/0095142 A1 Mar. 20, 2025

(51) Int. Cl.
*G06T 7/00* (2017.01)
*G06T 3/40* (2024.01)
(Continued)

(52) U.S. Cl.
CPC .............. *G06T 7/0012* (2013.01); *G06T 3/40* (2013.01); *G06T 5/70* (2024.01); *G16H 30/20* (2018.01);
(Continued)

(58) Field of Classification Search
CPC ........... G06T 3/40; G06T 5/70; G06T 7/0012; G06T 2207/10088; G06T 2207/20081; G06T 2207/20084; G06T 2211/424; G06T 3/4053; G06T 5/73; G06T 5/60; G06T 2207/30004; G06T 2207/20004; G06T 2207/30168; G06T 2211/441; G06T 2210/41; G06T 3/4076; G06T 2207/20182; A61B 6/5258; A61B 2576/00; A61B 5/7203; A61B 6/5211; A61B 5/0013; G06N 3/08; G06N 3/0464; G06N 20/00; G16H 30/20; G16H 30/40; G16H 30/00
See application file for complete search history.

(56) References Cited

U.S. PATENT DOCUMENTS 9,202,261 B2 * 12/2015 Ma ............................ G06T 5/70
10,949,951 B2 * 3/2021 Tang ...................... G06N 20/00
(Continued)

FOREIGN PATENT DOCUMENTS

CN 111127356 A * 5/2020 ............. G06N 3/045
CN 108828481 B * 1/2021 ......... G01R 33/5619
KR 20220165121 A * 12/2022 ........... G06T 3/4053

OTHER PUBLICATIONS

Y. Wang, Y. Deng, Y. Shen and H. Jin, "A New Concept of Multiple Neural Networks Structure Using Convex Combination," in IEEE Transactions on Neural Networks and Learning Systems, vol. 31, No. 11, pp. 4968-4979, Nov. 2020, doi: 10.1109/TNNLS.2019.2962020 (Year: 2020).*
(Continued)

*Primary Examiner* — Courtney Joan Nelson

(57) ABSTRACT

Systems and methods for image restoration of medical imaging data using an incremental process. The image restoration problem is decomposed into a sequence of intermediate steps that are easier to process than a single large step directly from the input to an output. Intermediate reconstructions are generated iteratively which provide for mapping a low-quality input to a high-quality reconstruction through a sequence of slightly less corrupted images.

17 Claims, 4 Drawing Sheets

(51) Int. Cl.
*G06T 5/70* (2024.01)
*G16H 30/20* (2018.01)
*G16H 30/40* (2018.01)

(52) U.S. Cl.
CPC ... *G16H 30/40* (2018.01); *G06T 2207/10088* (2013.01); *G06T 2207/30168* (2013.01)

(56) References Cited

U.S. PATENT DOCUMENTS

| | | | | |
|---|---|---|---|---|
| 2019/0347772 | A1* | 11/2019 | Zhang | G01R 33/565 |
| 2021/0390694 | A1* | 12/2021 | Mao | G16H 30/40 |
| 2022/0107378 | A1* | 4/2022 | Dey | G01R 33/56 |
| 2022/0188602 | A1* | 6/2022 | Meyer | G06N 3/045 |
| 2022/0395188 | A1* | 12/2022 | Shirai | G01R 33/5608 |

OTHER PUBLICATIONS

Machine translation obtained from Google Patents of CN-111127356-A (Year: 2020).*

Machine translation obtained from Google Patents of CN-108828481-B (Year: 2021).*

Machine translation of KR-20220165121-A obtained from Google Patents (Year: 2022).*

G. Sainarayanan, R. Nagarajan, C. D. Raman and M. Phanindranath, “Iterative image deblurring approach for coronary artery enhancement in MRI image,” 2005 1st International Conference on Computers, Communications, & Signal Processing with Special Track on Biomedical Engineering, Kuala Lumpur, Malaysia (Year: 2005) 005, pp. 320-323, doi: 10.1109/CCSP.2005.4977216. (Year: 2005).*

Chen, Yuhua, et al., “MRI super-resolution with GAN and 3D multi-level DenseNet: smaller, faster, and better”; arXiv preprint arXiv:2003.01217; 2020; pp. 1-22.

Hammernik, Kerstin, et al.; “Physics-driven deep learning for computational magnetic resonance imaging”, arXiv preprint arXiv:2203.12215, 2022, pp. 1-37.

Kong, Fangyuan, et al.; “Residual local feature network for efficient super-resolution”; Proceedings of the IEEE/CVF Conference on Computer Vision and Pattern Recognition, 2022; pp. 1-11.

Lee, Sangyun, et al.; “Progressive deblurring of diffusion models for coarse-to-fine image synthesis”; arXiv preprint arXiv:2207.11192, 2022; pp. 1-10.

Lv, Jun, Chengyan Wang, and Guang Yang; “PIC-GAN: a parallel imaging coupled generative adversarial network for accelerated multi-channel MRI reconstruction”; Diagnostics 11, 61; 2021, pp. 1-15.

Ran, Maosong, et al., “Denoising of 3D magnetic resonance images using a residual encoder-decoder Wasserstein generative adversarial network”; Medical image analysis 55, 2019; pp. 165-180.

Saharia, Chitwan, et al.; “Image super-resolution via iterative refinement”; IEEE Transactions on Pattern Analysis and Machine Intelligence; 2022, pp. 1-28.

Whang, Jay, et al.; “Deblurring via stochastic refinement”; Proceedings of the IEEE/CVF Conference on Computer Vision and Pattern Recognition; 2022; pp. 1-28.

Ye, Mao, Lemeng Wu, and Qiang Liu. “First hitting diffusion models for generating manifold, graph and categorical data.” Advances in Neural Information Processing Systems 35 (2022): 27280-27292.

Zhan, Bo, et al.; “Multi-modal MRI image synthesis via GAN with multi-scale gate mergence”; IEEE Journal of Biomedical and Health Informatics 26.1, 2021; pp. 17-26.

* cited by examiner

ITERATIVE RESTORATION OF CORRUPTED MR IMAGES

FIELD

This disclosure relates to medical imaging, such as image restoration in magnetic resonance (MR) imaging.

BACKGROUND

Magnetic resonance imaging (MRI) is an important and useful imaging modality used in clinical practice. MRI is a non-invasive imaging technology that produces three dimensional detailed anatomical images. It is often used for disease detection, diagnosis, and treatment monitoring. Regardless of the care practiced in acquiring the image data, artifacts might still exist, such as noise and blur. Such artifacts can complicate subsequent analysis of the data. Restoration or reconstruction of such corrupted MRI using certain techniques such as denoising or deblurring includes an ill-posed inverse problem where multiple high-quality reconstructions are plausible reconstructions of a given low-quality input. Typically, the correction of such artifacts is a tradeoff between resulting noise, blurring, low contrast at interfaces, and spatial resolution. Current approaches that are used to solve such a problem use single step supervised deep learning (DL) models. These approaches tend to produce blurry and unrealistic reconstructions as an aggregation of all plausible reconstructions. Hence, there is still a need for alternative DL solutions that avoid converging to the mean or median of the given training datasets.

SUMMARY

By way of introduction, the preferred embodiments described below include methods, systems, instructions, and computer readable media for iteratively improving image restoration in incremental steps, resulting in final restorations with more satisfactory perceptual quality.

In a first aspect, a method for image restoration, the method comprising: acquiring medical imaging data; inputting the medical imaging data into an iterative restoration network, the iterative restoration network configured to output higher quality medical imaging data using multiple incremental steps that provide a sequence of slightly less corrupted images; and outputting, by the iterative restoration network, the higher quality medical imaging data.

In a second aspect, a system for image restoration, the system comprising: a medical imaging device configured to acquire medical imaging data of a patient; an iterative restoration network with a plurality of stages trained using machine learning, each stage of the plurality of stages configured to incrementally improve a quality of input image data from a previous stage; and a processor configured to apply the iterative restoration network to medical imaging data from the medical imaging device and to provide a representation of the patient based on an output of the iterative restoration network.

In a third aspect, a non-transitory computer readable storage medium comprising a set of computer-readable instructions stored thereon which, when executed by at least one processor cause the processor to: acquire medical imaging data; input the medical imaging data into an iterative restoration network, the iterative restoration network configured to output higher quality medical imaging data using a plurality of incremental steps that provide a sequence of slightly less corrupted images; and output, by the iterative restoration network, higher quality medical imaging data.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
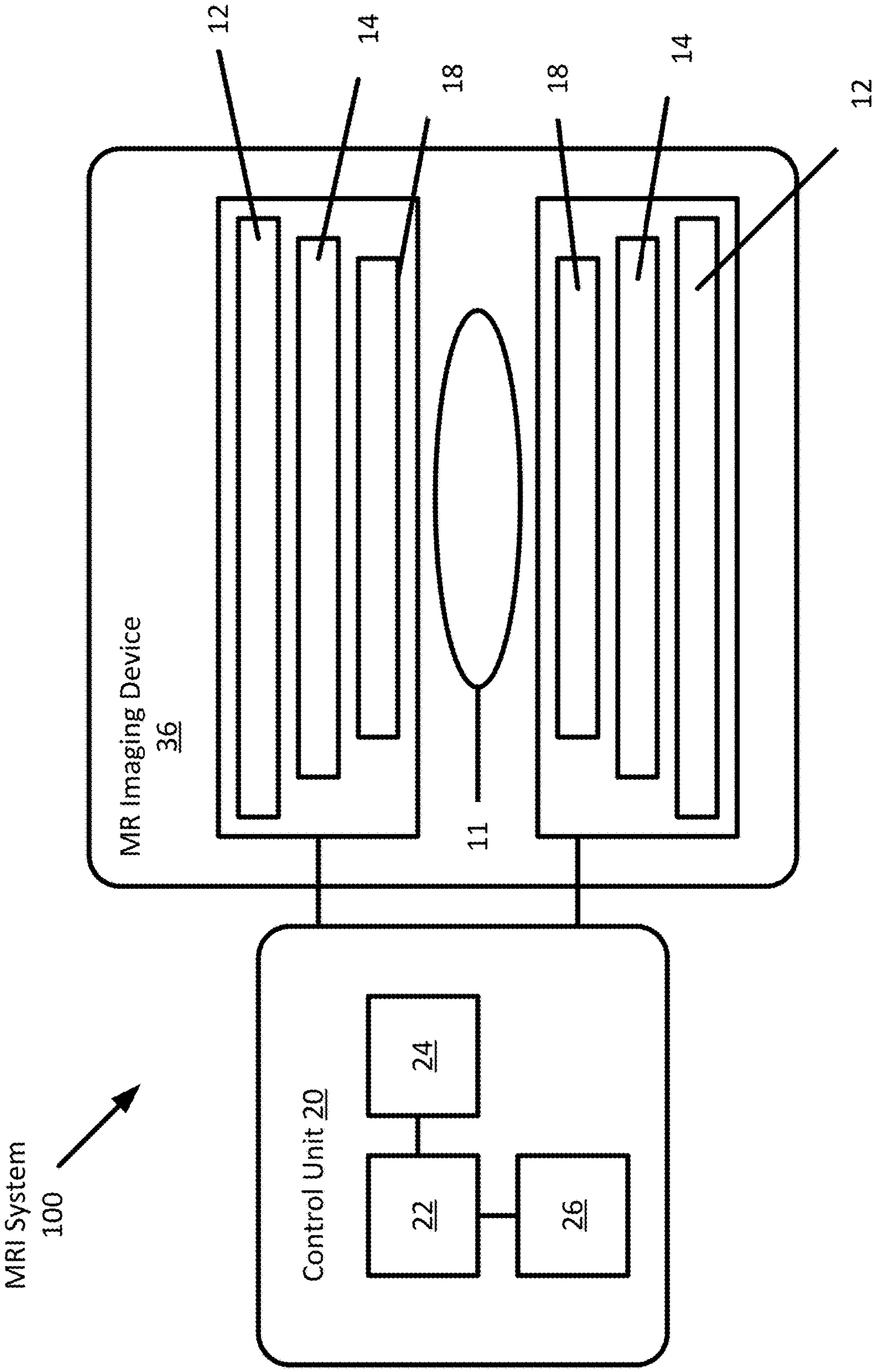
FIG. 1 depicts an example system for iterative restoration of MR images according to an embodiment.

Embodiments provide systems and methods for image restoration of medical imaging data using an incremental process. The image restoration problem is decomposed into a sequence of intermediate steps with less ill-posed tasks that are easier to process than a single large step directly from the input to an output. Intermediate reconstructions are generated iteratively which provide for mapping a low-quality input to a high-quality reconstruction through a sequence of slightly less corrupted images. The Intermediate steps may be defined as a convex combination of the input/ground truth images to simplify the mapping from low-quality images to high-quality ones.

Image restoration/reconstruction is the process of recovering or improving an image that has been degraded by noise, blur, or other distortions. It is a common task in medical image processing in order to improve an output for further analysis or review by medical personal. Image restoration, however, is not straightforward as it often involves solving ill-posed inverse problems, where the original image and the degradation process are unknown or partially known. In ill-posed inverse problems, restored images may not naturally appear with missing details or small structures due to the regression to the mean/median effect when L2 or L1 losses are used. To overcome this, additional loss terms have been proposed to balance the loss function, so the final reconstruction has an improved perceptual quality. In an example, adversarial losses have been used in MRI restoration tasks to improve the recovery of small structures. These approaches may only improve perceptual quality to a certain extent without completely recovering small structures. Moreover, the overall training becomes challenging regarding computational power and memory requirements. In addition, there is also an increased risk of introducing hallucinations.

Embodiments described herein address the problem of supervised DL reconstruction of ill-posed restoration tasks with an approach that does not try to predict the high-quality reconstruction in a single step but instead iteratively improving the reconstruction in incremental steps, resulting in final reconstructions with more satisfactory perceptual quality. While embodiments are described with reference to MRI, the mechanisms may also be applied to image restoration of imaging modalities use cases other than MRI (e.g., Computed tomography, X-ray, etc.).

The advantages of using the described embodiments compared to previous approaches include an ability to generate realistic reconstructions with improved perceptual image quality without the need for adversarial (i.e., GAN-based) losses that are hard to train with runs the risk of adding artificial structures to the final reconstruction (i.e., hallucinations). In addition, unlike Denoising Diffusion Probabilistic Models (DDPMs), embodiments do not require prior knowledge of the degradation process. Instead, an iterative restoration process is learned from low-quality/high-quality paired samples. Unlike Conditional DDPM models (cDDPM) the described embodiments are more efficient as the embodiments don't require starting the restoration process from pure noise (conditioned on input image) but instead directly iteratively restoring the input image. The flexibility of the proposed methods allows for a wide range of image restoration tasks (e.g., image denoising, image super-resolution, image artifact removal, image-to-image translation, motion correction, and accelerated kspace-image reconstruction) with applicability with different imaging modalities (e.g., CT, Xray, etc.) beyond MRI.

FIG. 1 depicts an example system 100 for iterative image restoration. This example is in a magnetic resonance context (i.e., a magnetic resonance scanner), but the masking in iterative reconstruction may be used in reconstruction for CT, PET, SPECT, or other medical imaging. In this example, MRI data is acquired by the MR system 100. The MRI data may be corrupted by noises and blurred during the acquisition. The goal of the image restoration process is to obtain clearer or cleaner images from noisy, blurred ones. The systems and methods described below may be used for reconstruction, denoising, deblurring, super resolution, etc. of any medical imaging data, for example, acquired by the MR imaging device 36 or other medical imaging device.

The MR system 100 includes an MR scanner 36 or system, a computer based on data obtained by MR scanning, a server, or another processor 22. The MR imaging device 36 is only exemplary, and a variety of MR scanning systems can be used to collect the MR data. The MR imaging device 36 (also referred to as a MR scanner or image scanner) is configured to scan a patient 11. The scan provides scan data in a scan domain. The MR imaging device 36 scans a patient 11 to provide k-space measurements (measurements in the frequency domain).

The MR system 100 further includes a control unit 20 configured to process the MR signals and generate images of the object or patient 11 for display to an operator. The control unit 20 includes a processor 22 that is configured to execute instructions, or the method described herein. The control unit 20 may store the MR signals and images in a memory 24 for later processing or viewing. The control unit 20 may include a display 26 for presentation of images to an operator.

In the MR system 100, magnetic coils 12 create a static base or main magnetic field B0 in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18. The RF coil 18 produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g., signals from the excited protons within the body as the protons return to an equilibrium position established by the static and gradient magnetic fields. The MR signals are detected and processed by a detector within RF module and the control unit 20 to provide an MR dataset to a processor 22 for processing into an image. In some embodiments, the processor 22 is located in the control unit 20, in other embodiments, the processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a non-cartesian or other spatial acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field generator acquires individual frequency components in an order corresponding to a sequence of substantially adjacent individual data elements in the array, and magnetic field gradient change between successively acquired frequency components is substantially minimized.

The control unit 20 may use information stored in an internal database to process the detected MR signals in a coordinated manner to generate high quality images of a selected slice(s) of the body (e.g., using the image data processor) and adjusts other parameters of the system 100. The stored information includes a predetermined pulse sequence of an imaging protocol and a magnetic field gradient and strength data as well as data indicating timing, orientation, and spatial volume of gradient magnetic fields to be applied in imaging.

The MR imaging device 36 is configured by the imaging protocol to scan a region of a patient 11. For example, in MR, such protocols for scanning a patient 11 for a given examination or appointment include diffusion-weighted imaging (acquisition of multiple b-values, averages, and/or diffusion directions), turbo-spin-echo imaging (acquisition of multiple averages), or contrast. In one embodiment, the protocol is for compressed sensing.

The system 100 may include an operator interface that is coupled to the control unit 20. The operator interface may include an input interface and an output interface. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. The output is a display device but may be an interface. The final and/or intermediate MR images reconstructed from the scan are displayed. For example, an image of a region of the patient 11 is displayed. A generated image of the reconstructed representation for a given patient 11 is presented on a display of the operator interface. The display 26 is a CRT, LCD, plasma, projector, printer, or other display device. The display is configured by loading an image to a display plane or buffer. The display is configured to display the reconstructed MR image of the region of the patient 11. The processor 22 of the operator interface forms a graphical user interface (GUI) enabling user interaction with MR imaging device 36 and enables user modification in substantially real time. The control unit 20 processes the magnetic resonance signals to provide image representative data for display on the display 26, for example.

The processor 22 reconstructs a representation of the patient 11 from the k-space data. Different reconstruction processes may be used depending on the type of sequence used. The processor 22 is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction. The processor 22 is a single device, a plurality of devices, or a network. For more than one device, parallel or sequential division of processing may be used. Different devices making up the processor 22 may perform different functions, such as reconstructing by one device and volume rendering by another device. In one embodiment, the processor 22 is a control processor or other processor of the MR system 100. Other processors of the MR system 100 or external to the MR system 100 may be used. The processor 22 is configured by software, firmware, and/or hardware to reconstruct. The instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor 22 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The processor 22 is configured for image restoration of an image. The image restoration may include or be part of the reconstruction from the k-space data. The reconstructed image may also be restored. Image restoration may include, for example image deblurring, super resolution, and denoising among other applications. Image deblurring is the process of fixing or generating a non-blurry image from a blurry image or image data. Denoising is the process of removing noise from an image. Super resolution is the process of enhancing the resolution of an image from low-resolution (LR) to high resolution (HR). Image restoration may include or be based on one or more inverse problems. In an inverse problem conclusions about the cause are taken from its observed (measured) effect. These tasks may be ill-posed, that is, small changes (for example, noisy measurements) in the effects lead to dramatic changes in the corresponding causes. Reconstructing a unique solution that fits the observations is difficult or impossible without some prior knowledge about the data. Traditional methods minimize a cost function that consists of a data-fit term, which measures how well the reconstructed image matches the observations, and a regularizer, which reflects prior knowledge and promotes images with desirable properties like smoothness. However, these restored images may remove or miss details or small structures due to the regression to the mean/median effect when L2 or L1 losses are used. Additional loss terms have been proposed to balance the loss function, so that the final reconstruction has improved perceptual quality. In an example, using a GAN, adversarial losses have been used in MRI restoration tasks to improve the recovery of small structures. However, this approach may only improve perceptual quality to a certain extent without completely recovering small structures. In addition, the overall training of such models becomes challenging regarding computational power and memory requirements. The processor 22 is configured to provide supervised DL of the ill-posed restoration tasks by not predicting a high-quality reconstruction in a single step but instead iteratively improving the reconstruction in incremental steps, resulting in final reconstructions with more satisfactory perceptual quality. The restoration task may include reconstruction, denoising, deblurring, super resolution, among other ill posed tasks.

Figure 2:
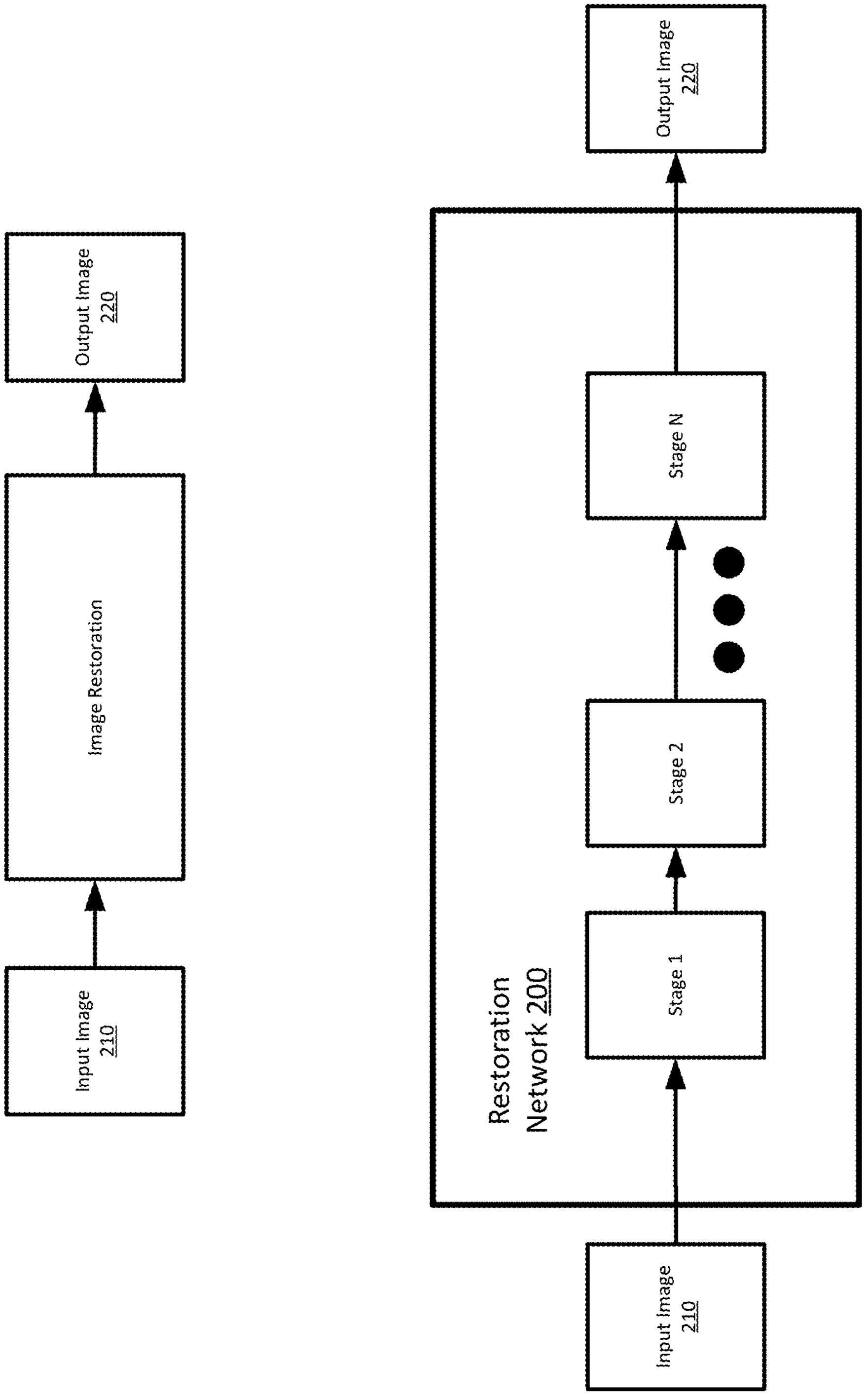
FIG. 2 depicts an example of a classical restoration process and an iterative restoration process according to an embodiment.

FIG. 2 depicts an example of a classical restoration process (top) and an incremental restoration process (bottom). In a classical restoration process, an image 210 is input into a restoration network that processes the image 210 and outputs a higher quality image 220 in what can be considered a single step. Such a restoration network may include multiple components or layers but is considered to be a single component to the operator. For example, the restoration network may be trained end to end. Any intermediary results are not seen or adjusted by an operator. Instead of a single step, embodiments provide where the restoration process is broken into different stages or steps. In the bottom process of FIG. 2, N steps are depicted for the iterative restoration network 200, but more or less may be used. Each step inputs the output from the previous stage and performs incremental restoration. In an example, the classical restoration network performs 100% of the denoising of an image in a single step. In the incremental restoration each stage only performs a percentage of the denoising, for example one sixth of the total if there are six stages. After the first stage, the image is 1/6 denoised. After the second stage, the image is 2/6 denoised, etc. The amount of denoising by each stage may be equal or may increase or decrease over time. In an example, the level of denoising may be heavy at the first few stages but then become less and less as the subsequent stages perform finer tuned denoising.

The incremental process provides an ability to generate realistic reconstructions with improved perceptual image quality without the need for adversarial (i.e., GAN-based) losses that are hard to train with runs the risk of adding artificial structures to the final reconstruction (i.e., hallucinations). In addition, unlike Denoising Diffusion Probabilistic Models (DDPMs), the incremental steps do not require prior knowledge of the degradation process. Instead, an iterative restoration process is learned from low-quality/high-quality paired samples. Unlike Conditional DDPM models (cDDPM), the incremental steps are more efficient as they don't require starting the restoration process from pure noise (conditioned on input image) but instead directly iteratively restoring the input image. The flexibility of the incremental restoration network 200 allows for a wide range of image restoration tasks (e.g., image denoising, image super-resolution, image artifact removal, image-to-image translation, motion correction, and accelerated kspace-image reconstruction) with applicability with different imaging modalities (e.g., CT, Xray, etc.) beyond MRI.

As noted, the training of the restoration network 200 is not done end to end, but rather each stage is trained as an iterative block. In an embodiment, a machine-learned model such as a CNN is used for at least part of the restoration, such as for regularization. In regularization, the image or object domain data is input, and an image or object domain data with less artifact is output. The remaining portions or stages of the reconstruction/restoration (e.g., non-uniform Fast Fourier transform and gradients in iterative optimization) are performed using reconstruction algorithms and/or other machine-learned networks. In other embodiments, a machine-learned model is used for all the reconstruction/restoration operations (one model to input k-space data and output regularized image data) or other reconstruction operations (e.g., used for transform, gradient operation, and/or regularization). The reconstruction is of an object or image domain from projections or measurements in another domain, and the machine-learned model is used for at least part of the reconstruction.

In an embodiment, the processor 22 is configured to provide a representation in an object domain. The representation or object in the object domain may be reconstructed from the scan data in the scan domain. The scan data is a set or frame of k-space data from a scan of the patient 11. The object domain is an image space and corresponds to the spatial distribution of the patient 11. A planar or volume representation or object is reconstructed as an image representing the patient 11. For example, pixels values representing tissue in an area or voxel values representing tissue distributed in a volume are generated. The reconstruction is performed, at least in part, using a machine-learned model or algorithm. The input k-space data, for example, is input into the restoration network 200.

The goal of the restoration network 200 when configured for denoising is to iteratively transform the input into a cleaner less noisy image by gradually refining the noise through a series of incremental steps. The incremental steps involve applying a sequence of learned transformations to the input. At each incremental step, the restoration network 200 learns to transform the input by introducing a certain amount of noise into the current state. The noise acts as a source of randomness that helps explore the data distribution and progressively reveal the underlying patterns. The amount of noise added may gradually decrease as the steps progress, leading to a refined representation.

The training process for the restoration network 200 includes optimizing the restoration network 200 to minimize the difference between the generated samples and the actual data. This is accomplished by maximizing the probability of the observed data within the restoration network framework. During an inference phase, the restoration network 200 may generate new samples by running the process in reverse. Given a trained model and an initial image, the model applies the reverse transformations to gradually remove the noise and generate a sample that resembles the training data. In an embodiment, the training of a stage of the restoration network 200 using a convex combination formulation.

Different neural network configurations and workflows may be used for the restoration network 200 such as a convolution neural network (CNN), deep belief nets (DBN), or other deep networks. CNN learns feed-forward mapping functions while DBN learns a generative model of data. In addition, CNN uses shared weights for all local regions while DBN is a fully connected network (e.g., including different weights for all regions of a feature map. The training of CNN is entirely discriminative through back-propagation. DBN, on the other hand, employs the layer-wise unsupervised training (e.g., pre-training) followed by the discriminative refinement with backpropagation if necessary. In an embodiment, the arrangement of the trained network is a fully convolutional network (FCN). Alternative network arrangements may be used, for example, a three-dimensional Very Deep Convolutional Networks (3D-VGGNet). VGGNet stacks many layer blocks containing narrow convolutional layers followed by max pooling layers. A three-dimensional Deep Residual Networks (three-dimensional-ResNet) architecture may be used. A Resnet uses residual blocks and skip connections to learn residual mapping. The training data (and other networks) includes ground truth data or gold standard data. Different training data may be acquired and annotated.

Figure 3:
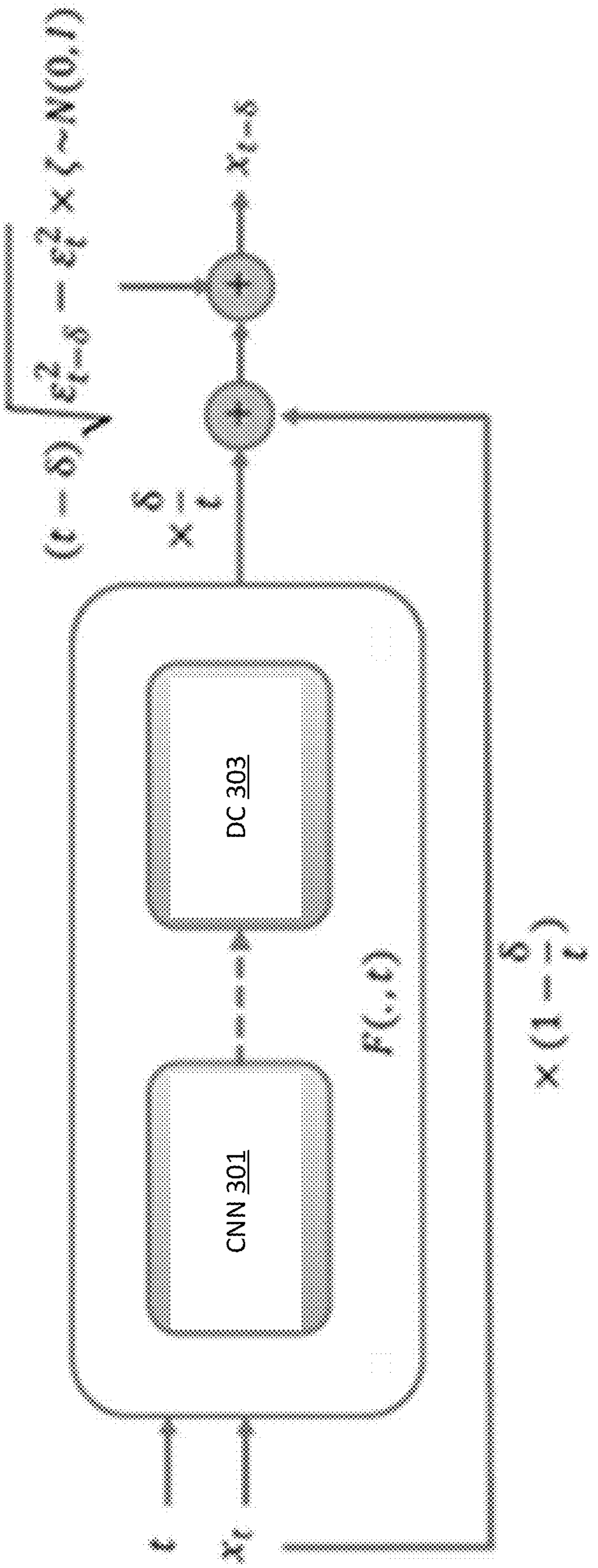
FIG. 3 depicts an example of an example stage of the iterative restoration process according to an embodiment.

FIG. 3 depicts an example of an iterative restoration process at inference time. FIG. 3 depicts a stage of the iterative restoration network 200. The stage includes a CNN 302 and a DC layer 303. The recovery process starts with the input low-quality image (time t=1), and then at a given time-step, t generates the best possible reconstruction at time $t-\delta$. This process is repeated till (time t=0), inverting the total degradation incrementally. The step $0<\delta\leq 1$ controls the rate of the restoration process, which can be defined as a function of time or defined as a constant speed $$\left(\text{i.e, } \delta = \frac{1}{M}\right)$$

where M is the total number of iterations).

In an embodiment, a physics-driven deep learning model using a lightweight CNN and data consistency layers may be used to solve the defined, less ill-posed intermediate restoration tasks. Using a convex combination formulation, intermediate reconstructions are defined as:

$$x_{t-\delta} = \frac{\delta}{t}F(x_t, t) + \left(1 - \frac{\delta}{t}\right)x_t.$$

The convex combination may be a linear combination of points where all coefficients are non-negative and sum to 1.

A first function describes the initial image, and a second function describes the target image. A convex combinations of these functions describes a continuous deformation of the initial image into the target shape.

To better guide the restoration process particularly in the presence of deterministic degradations, a small amount of white noise may be added as a constant value ε or a function of time $\varepsilon_t$) to the iterative process output as:

$$x_{t-\delta} = \frac{\delta}{t}F(x_t, t) + \left(1 - \frac{\delta}{t}\right)x_t + (t-\delta)\sqrt{\varepsilon_{t-\delta}^2 - \varepsilon_t^2} \times \zeta \sim N(0, I)$$

In the example network of FIG. 3, the CNN 301 may be any type of CNN that performs regularization. In one embodiment, deep learning is used to train the restoration network 200. Machine learning uses an offline training phase where the goal is to identify an optimal set of values of learnable parameters of the model/network that can be applied to many different inputs (i.e., image domain data after gradient calculation in the optimization or minimization of the reconstruction). The machine-learned parameters may subsequently be used during clinical operation to rapidly reconstruct images. Once learned, the machine-learned model is used in an online processing phase in which MR scan data y (e.g., k-space measurements) for patients is input and the reconstructed representations for the patients are output based on the model values learned during the training phase. Other functions may use machine-learned models or networks. During application to one or more different patients and corresponding different measurements, the same learned weights or values for the machine-learned network are used for each iteration. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, retrained, or replaced but does not learn new values as part of application for a given patient.

The example CNN 301 of FIG. 3 includes an architecture that defines the learnable variables and the relationships between the variables. In one embodiment for the regularization, a neural network is used, but other networks may be used. Any number of layers and nodes within layers may be used. A DenseNet, U-Net, encoder-decoder, Deep Iterative Down-Up CNN, and/or another network may be used. In one embodiment, an image-to-image neural network (spatial distribution input and spatial distribution output) is used. The image-to-image neural network may include convolution layers or be a CNN. Some of the network may include dense blocks (i.e., multiple layers in sequence outputting to the next layer as well as the final layer in the dense block). Any known or later developed neural network may be used.

Deep learning is used to train the model for each iteration where machine learning is used. The training learns both the features of the input data and the conversion of those features to the desired output (i.e., denoised or regularized image domain data). Backpropagation, RMSprop, ADAM, or another optimization is used in learning the values of the learnable parameters. The incremental steps involve applying a sequence of learned transformations to the input. At each incremental step, the restoration network 200 learns to transform the input by introducing a certain amount of noise into the current state. The noise acts as a source of randomness that helps explore the data distribution and progressively reveal the underlying patterns. The amount of noise added may gradually decrease as the steps progress, leading to a refined representation.

The training process for the restoration network 200 includes optimizing the restoration network 200 to minimize the difference between the generated samples and the actual data. This is accomplished by maximizing the probability of the observed data within the restoration network framework. During an inference phase, the restoration network 200 may generate new samples by running the process in reverse. Given a trained model and an initial image, the model applies the reverse transformations to gradually remove the noise and generate a sample that resembles the training data. In an embodiment, the training of a stage of the restoration network 200 using a convex combination formulation. Where the training is supervised, the differences (e.g., L1, L2, or mean square error) between the estimated output and the ground truth output are minimized. Joint training (e.g., semi-supervised) may be used. In the example network of FIG. 3, given a low-quality sample x and a corresponding high-quality sample x from the training dataset, the deep learning model is trained in supervised setting to minimize the following loss function:

$$\left\|F\left((1-t)x + ty + t \sim U(0, I) \times \varepsilon_t \times n \sim N(0, I)\right)\right\|_p$$

Alternative training mechanisms or losses may be used depending on the type of image restoration, the type of input data, and the required output.

Figure 4:
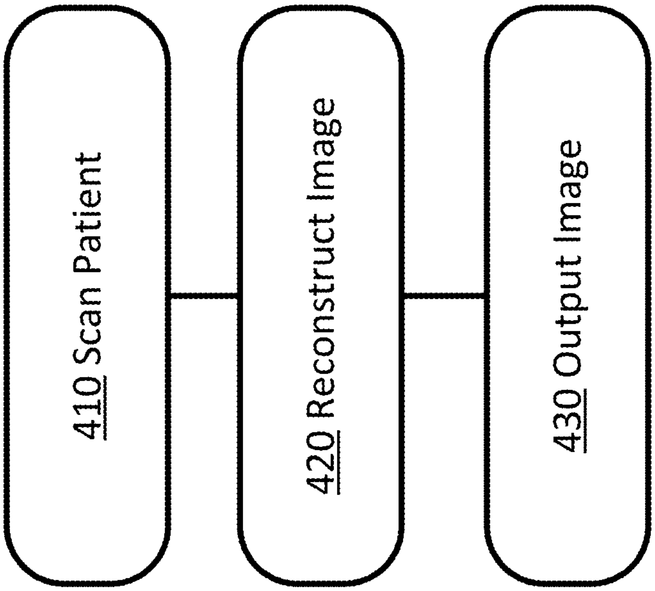
FIG. 4 depicts an example workflow for iterative reconstruction of an MR image according to an embodiment.

FIG. 4 is a flow chart diagram of one embodiment of a method for reconstruction of a medical image in a medical imaging system 100, such as reconstruction of a MR image in an MR system 100. The method is performed by the system 100 of FIG. 1 or another system and may use the CNN 301 and DC layer(s) 303 of FIG. 3. The medical scanner scans the patient 11. A representation is reconstructed from the k-space data using an image restoration network 200 that includes a plurality of incremental steps. The representation may be a medical image, A display displays the representation. Other components may be used, such as a remote server or a workstation performing the acquisition of the scan data, the reconstruction, and/or the display. The method is performed in the order shown or other orders. Additional, different, or fewer acts may be provided. For example, different preset, default, or user input settings are used to configure the scanning act 410. The output of the reconstruction process may be further processed or analyzed, for example by an addition neural network or model that is configured to further augment or process the image. As another example, the image is stored in a memory (e.g., computerized patient medical record) or transmitted over a computer network instead of or in addition to the display of act 430. The restoration network 200 may be configured for reconstruction such as accelerated kspace-image reconstruction, image denoising, image super-resolution, image artifact removal, image-to-image translation, and motion correction among other tasks. The process described below is an example of reconstruction. Reconstruction may include or provide denoising, deblurring, etc. For other tasks, different input data may be used, for example, a corrupted image. For these different tasks, different models may be used in the respective stages. For example, a model trained for denoising may be used for a restoration network 200 that is configured for denoising whereas a model trained for super-resolution may be used for a restoration network 200 that is configured for super-resolution.

In act 410, the imaging device 36 scans a patient 11. The scan is guided by a protocol, such as parallel imaging with compressed sensing or another protocol. The pulse or scan sequence scans the region of the patient 11, resulting in scan data for a single imaging appointment. In an MR example, a pulse sequence is created based on the configuration of the MR scanner (e.g., the imaging protocol selected). The pulse sequence is transmitted from coils into the patient 11. The resulting responses are measured by receiving radio frequency signals at the same or different coils. The scanning results in k-space measurements as the scan data.

At act 420, a restoration network 200 reconstructs an image from the imaging data acquired at act 410. The reconstruction uses, at least in part, a machine-learned model, such as a neural network trained with deep machine learning. The machine-learned model is previously trained, and then used as trained in reconstruction. Fixed values of learned parameters are used for application. The restoration network 200 includes a plurality of steps/stages that incrementally transform the input image to an output image.

In an embodiment, the restoration network 200 is configured for reconstruction. In another embodiment, the restoration network 200 is configured for denoising. In yet another embodiment, the restoration network 200 is configured for deblurring. Any of various machine-learned models may be used, such as a neural network or support vector machine. The machine-learned model is part of an iterative reconstruction that uses a plurality of incremental steps to reconstruct the image. The same machine-learned model or network (e.g., CNN) is used for each of the iterations. The learnable parameters of the architecture of the reconstruction network are trained for altering the characteristic or characteristics, such as for denoising (removing or reducing noise). In a compressed sensing embodiment, the ground truth representation for training may be reconstructions formed from full sampling, so having reduced noise. Other ground truth representations may be used, such as generated by simulation or application of a denoising or other characteristic altering algorithm. The training data includes many sets of data, such as representations output by reconstruction and the corresponding ground truth. Tens, hundreds, or thousands of samples are acquired, such as from scans of volunteers or patients, scans of phantoms, simulation of scanning, and/or by image processing to create further samples. Many examples that may result from different scan settings, patient anatomy, scanner characteristics, or other variance that results in different samples are used. In one embodiment, an already gathered or created MR dataset is used for the training data. The samples are used in machine learning (e.g., deep learning) to determine the values of the learnable variables (e.g., values for convolution kernels) that produce outputs with minimized cost or loss across the variance of the different samples.

In an example, the recovery process starts with the input low-quality image (time t=1), and then at a given time-step t generates the best possible reconstruction at time t−δ. The step 0<δ≤1 controls the rate of the restoration process, which can be defined as a function of time or defined as a constant speed $$\left(\text{i.e}, \delta = \frac{1}{M}\right)$$

where M is the total number of iterations). Physics-driven deep learning model F (•, t) utilizing lightweight CNNs and data consistency layers may solve the defined, less ill-posed intermediate restoration tasks. Using a convex combination formulation, intermediate reconstructions are defined as $$x_{t-\delta} = \frac{\delta}{t}F(x_t, t) + \left(1 - \frac{\delta}{t}\right)x_t.$$

To better guide the restoration process particularly in the presence of deterministic degradations, a small amount of white noise (for example a constant value ε or a function of time Et) to the iterative process output:

$$x_{t-\delta} = \frac{\delta}{t}F(x_t, t) + \left(1 - \frac{\delta}{t}\right)x_t + (t-\delta)\sqrt{\varepsilon_{t-\delta}^2 - \varepsilon_t^2} \times \zeta \sim N(0, I)$$

Given low-quality sample x and corresponding high-quality sample x from the training dataset, the deep learning model is trained in supervised setting to minimize the following loss function:

$$\left\| F\left((1-t)x + ty + t \sim U(0, I) \times \varepsilon_t \times n \sim N(0, I)\right\|_p$$

The restoration network 200 is machine trained using a supervised process and training data. In one embodiment, deep learning is used. Each stage of the restoration network 200 is configured to take the input image and gradually add noise to it through a series of steps. This is the forward process. The restoration network 200 is trained to recover the original data by reversing the denoising process. By being able to model the reverse process, the restoration network 200 can generate new data. This is the reverse diffusion process or, in general, the sampling process of a generative model. The rate of the restoration process may be fixed to a constant or chosen as a schedule over the stages. The rate may be linear, quadratic, cosine etc.

The training learns both the features of the input data and the conversion of those features to the desired output. Backpropagation, RMSprop, ADAM, or other optimization may be used in learning the values of the learnable parameters of the network (e.g., the convolutional neural network (CNN) or fully connection network (FCN)). Where the training is supervised, the differences (e.g., L1, L2, mean square error, or other loss) between the estimated output and the ground truth output are minimized.

Any architecture or layer structure for machine learning to perform an operation for separately reconstructing from subsets may be used. For example, any of the architectures may be used. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, image-to-image and/or another network may be used. Some of the network may include dense blocks (i.e., multiple layers in sequence outputting to the next layer as well as the final layer in the dense block). Any known or later developed neural network may be used. Any number of hidden layers may be provided between the input layer and output layer.

The reconstruction may output the representation as pixels, voxels, and/or a display formatted image in response to the input. Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

In act 430 of FIG. 4, the processor 22 generates and displays an image of the object from the output representation. The resulting representation or image may be rendered to a two-dimensional display. A display (e.g., display screen or device) displays the medical image, such as the MR image, a series of images (over time), and/or a 3D volume generated from multiple images or slices. The medical image, after or as part of any post processing, is formatted for display on the display. The display presents the image for viewing by the user, radiologist, physician, clinician, and/or patient 11. The image assists in diagnosis, prognosis, and/or therapy. The displayed image may represent a planar region or area in the patient 11. Alternatively, or additionally, the displayed image is a volume or surface rendering from voxels (three-dimensional distribution) to the two-dimensional display.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The following is a list of non-limiting illustrative embodiments disclosed herein:

Illustrative embodiment 1. A method for image restoration, the method comprising: acquiring medical imaging data; inputting the medical imaging data into an iterative restoration network, the iterative restoration network configured to output higher quality medical imaging data using multiple incremental steps that provide a sequence of slightly less corrupted images; and outputting, by the iterative restoration network, the higher quality medical imaging data.

Illustrative embodiment 2. The method of illustrative embodiment 1, wherein the medical imaging data is acquired using a magnetic resonance imaging device.

Illustrative embodiment 3. The method according to one of the preceding embodiments, wherein the iterative restoration network is configured to reconstruct a high-resolution image from a low-resolution image.

Illustrative embodiment 4. The method according to one of the preceding embodiments, wherein the iterative restoration network is configured to denoise the medical imaging data.

Illustrative embodiment 5. The method according to one of the preceding embodiments, wherein each incremental step includes a CNN and a data consistency layer.

Illustrative embodiment 6. The method according to one of the preceding embodiments, wherein a rate of restoration at each incremental step is controlled by a predefined parameter.

Illustrative embodiment 7. The method according to illustrative embodiment 6, wherein the predefined parameter is defined as a function of time or as a constant speed.

Illustrative embodiment 8. The method according to one of the preceding embodiments, wherein the iterative restoration network is trained by optimizing a loss of a convex combination of input and ground truth images.

Illustrative embodiment 9. The method according to one of the preceding embodiments, wherein an amount of white noise is added to an output of each incremental step.

Illustrative embodiment 10. A system for image restoration, the system comprising: a medical imaging device configured to acquire medical imaging data of a patient; an iterative restoration network with a plurality of stages trained using machine learning, each stage of the plurality of stages configured to incrementally improve a quality of input image data from a previous stage; and a processor configured to apply the iterative restoration network to medical imaging data from the medical imaging device and to provide a representation of the patient based on an output of the iterative restoration network.

Illustrative embodiment 11. The system of illustrative embodiment 10, wherein the medical imaging device comprises a magnetic resonance imaging device.

Illustrative embodiment 12. The system according to one of the preceding embodiments, wherein the iterative restoration network is configured to reconstruct a high-resolution image from a low-resolution image.

Illustrative embodiment 13. The system according to one of the preceding embodiments, wherein the iterative restoration network is configured to denoise the medical imaging data.

Illustrative embodiment 14. The system according to one of the preceding embodiments, wherein a rate of an incremental improvement by each stage of the plurality of stages is controlled by a predefined parameter.

Illustrative embodiment 15. The system according to illustrative embodiment 14, wherein the predefined parameter is defined as a function of time or as a constant speed.

Illustrative embodiment 16. The system according to one of the preceding embodiments, wherein the iterative restoration network is trained by optimizing a loss of a convex combination of input and ground truth images.

Illustrative embodiment 17. A non-transitory computer readable storage medium comprising a set of computer-readable instructions stored thereon which, when executed by at least one processor cause the processor to: acquire medical imaging data; input the medical imaging data into an iterative restoration network, the iterative restoration network configured to output higher quality medical imaging data using a plurality of incremental steps that provide a sequence of slightly less corrupted images; and output, by the iterative restoration network, higher quality medical imaging data.

Illustrative embodiment 18. The non-transitory computer readable storage medium according to illustrative embodiment 17, further comprising instructions to: display the higher quality medical imaging data.

Illustrative embodiment 19. The non-transitory computer readable storage medium according to one of the preceding embodiments, wherein the higher quality medical imaging data includes less noise, is less blurry, or includes less noise and is less blurry than the input image data.

Illustrative embodiment 20. The non-transitory computer readable storage medium according to one of the preceding embodiments, wherein a rate of each incremental step of the plurality of incremental steps is controlled by a predefined parameter.

The invention claimed is:

1. A method for image restoration, the method comprising:

acquiring medical imaging data;

inputting the medical imaging data into an iterative restoration network configured to solve an ill-posed inverse image restoration problem by progressively reversing image degradation through a plurality of trained restoration stages, each restoration stage of the plurality of trained restoration stages trained to perform a partial restoration that reduces image corruption relative to an output of a previous stage, the iterative restoration network configured to generate a sequence of intermediate images corresponding to progressively less degraded reconstructions of the medical imaging data, wherein each restoration stage includes generating an intermediate image of the sequence of intermediate images using a convolutional neural network (CNN) and a data consistency layer; and outputting, by the iterative restoration network, higher quality medical imaging data corresponding to a final restoration stage of the plurality of trained restoration stages.

2. The method of claim 1, wherein the medical imaging data is acquired using a magnetic resonance imaging device.

3. The method of claim 1, wherein the iterative restoration network is configured to reconstruct a high-resolution image from a low-resolution image.

4. The method of claim 1, wherein the iterative restoration network is configured to denoise the medical imaging data.

5. The method of claim 1, wherein a rate of restoration at each restoration stage is controlled by a predefined parameter.

6. The method of claim 5, wherein the predefined parameter is defined as a function of time or as a constant speed.

7. The method of claim 1, wherein the iterative restoration network is trained by optimizing a loss of a convex combination of input and ground truth images.

8. The method of claim 1, wherein an amount of white noise is added to an output of each restoration stage.

9. A system for image restoration, the system comprising:

a medical imaging device configured to acquire medical imaging data of a patient;

an iterative restoration network configured to solve an ill-posed inverse image restoration problem by progressively reversing image degradation through a plurality of different restoration stages, each restoration stage of the plurality of different restoration stages trained using machine learning to perform a partial restoration that reduces image corruption relative to an output of a previous stage of the plurality of different restoration stages, each stage of the plurality of different restoration stages configured to generate an intermediate image of a sequence of intermediate images corresponding to progressively less degraded reconstructions of the medical imaging data, wherein a rate of an incremental improvement by each stage of the plurality of different restoration stages is controlled by a predefined parameter; and a processor configured to apply the iterative restoration network to medical imaging data from the medical imaging device and to provide a representation of the patient based on an output of the iterative restoration network.

10. The system of claim 9, wherein the medical imaging device comprises a magnetic resonance imaging device.

11. The system of claim 9, wherein the iterative restoration network is configured to reconstruct a high-resolution image from a low-resolution image.

12. The system of claim 9, wherein the iterative restoration network is configured to denoise the medical imaging data.

13. The system of claim 9, wherein the predefined parameter is defined as a function of time or as a constant speed.

14. The system of claim 9, wherein the iterative restoration network is trained by optimizing a loss of a convex combination of input and ground truth images.

15. A non-transitory computer readable storage medium comprising a set of computer-readable instructions stored thereon which, when executed by at least one processor cause the processor to:

acquire medical imaging data;

input the medical imaging data into an iterative restoration network, the iterative restoration network configured to solve an ill-posed inverse image restoration problem by progressively reversing image degradation through a plurality of trained restoration stages, each restoration stage of the plurality of trained restoration stages trained using machine learning to perform a partial restoration that reduces image corruption relative to an output of a previous stage of the plurality of trained restoration stages, the iterative restoration network configured to generate a sequence of intermediate images corresponding to progressively less degraded reconstructions of the medical imaging data, wherein a rate of each restoration stage of the plurality of trained restoration stages is controlled by a predefined parameter; and output, by the iterative restoration network, higher quality medical imaging data corresponding to a final restoration stage of the plurality of trained restoration stages.

16. The non-transitory computer readable storage medium of claim 15, further comprising instructions to:

display the higher quality medical imaging data.

17. The non-transitory computer readable storage medium of claim 15, wherein the higher quality medical imaging data includes less noise, is less blurry, or includes less noise and is less blurry than the input image data.

* * * * *